United States Patent
Michon et al.

(10) Patent No.: US 6,372,222 B1
(45) Date of Patent: *Apr. 16, 2002

(54) ANTIGENIC GROUP B STREPTOCOCCUS TYPE II AND TYPE III POLYSACCHARIDE FRAGMENTS HAVING A 2, 5-ANHYDRO-D-MANNOSE TERMINAL STRUCTURE AND CONJUGATE VACCINE THEREOF

(75) Inventors: Francis Michon, Laurel, MD (US); Catherine Uitz, Arlington, VA (US); Joseph Y. Tai, Fort Washington, PA (US)

(73) Assignee: Baxter International Inc., Deerfield, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/025,225

(22) Filed: Feb. 18, 1998

Related U.S. Application Data

(62) Division of application No. 08/481,883, filed on Jun. 7, 1995.

(51) Int. Cl.[7] ............... A61K 39/385; A61K 39/09; A61K 39/02; A61K 39/116; A01N 43/04

(52) U.S. Cl. ............... 424/197.11; 424/244.1; 424/234.1; 424/193.1; 424/194.1; 424/203.1; 424/236.1; 424/184.1; 424/831; 514/23; 514/54; 536/123.1

(58) Field of Search ............... 424/184.1, 193.1, 424/194.1, 197.11, 203.1, 236.1, 244.1, 831, 234.1; 536/123.1; 530/402, 403; 514/23, 54

(56) References Cited

U.S. PATENT DOCUMENTS

| | | | |
|---|---|---|---|
| 3,352,773 A | * 11/1967 | Scwartz et al. | |
| 3,922,260 A | 11/1975 | Peniston et al. | 260/211 R |
| 4,207,414 A | 6/1980 | Kasper | 536/1 |
| 4,284,537 A | 8/1981 | Beachley | 260/6 |
| 4,324,887 A | 4/1982 | Kasper | 536/53 |
| 4,356,170 A | 10/1982 | Jennings et al. | 424/92 |
| 4,356,263 A | 10/1982 | Kasper | 435/101 |
| 4,367,221 A | 1/1983 | Kasper | 424/87 |
| 4,367,222 A | 1/1983 | Kasper | 424/87 |
| 4,367,223 A | 1/1983 | Kasper | 424/92 |
| 4,413,057 A | 11/1983 | Carlo et al. | 435/101 |
| 4,425,330 A | 1/1984 | Norcross et al. | 424/92 |
| 4,438,261 A | 3/1984 | Barnett | 536/21 |
| 4,500,519 A | * 2/1985 | Lormeau et al. | 514/56 |
| 4,619,828 A | 10/1986 | Gordon | 424/92 |
| 4,711,779 A | 12/1987 | Porro et al. | 424/92 |
| 4,757,134 A | 7/1988 | Blake et al. | 530/350 |
| 4,789,735 A | 12/1988 | Frank et al. | 530/395 |
| 4,902,506 A | 2/1990 | Anderson et al. | 424/92 |
| 5,302,386 A | 4/1994 | Kasper | 424/92 |
| 5,306,492 A | 4/1994 | Porro | 424/88 |
| 5,312,908 A | * 5/1994 | Nakao | 536/20 |
| 5,352,588 A | 10/1994 | Fischetti et al. | 435/69.1 |
| 5,439,808 A | * 8/1995 | Blake et al. | 435/69.1 |
| 5,536,646 A | * 7/1996 | Sand et al. | 435/36 |
| 5,766,606 A | * 6/1998 | Brady | 424/244.1 |

FOREIGN PATENT DOCUMENTS

| | | |
|---|---|---|
| EP | 0 175 261 | 3/1986 |
| EP | 0 206 852 | 12/1986 |
| EP | 0208375 | * 1/1987 |
| EP | 0 245 045 | 11/1987 |
| WO | 0 038 265 A1 | 10/1981 |
| WO | WO 8706267 | * 10/1987 |
| WO | WO 87/06267 | 10/1987 |
| WO | WO 89/00583 | 1/1989 |
| WO | WO 91/04049 | 4/1991 |
| WO | WO 91/04335 | 4/1991 |
| WO | WO 91/08772 | 6/1991 |
| WO | WO 92/17588 | 10/1992 |
| WO | WO 93/07178 | 4/1993 |
| WO | WO 94/06467 | 3/1994 |
| WO | WO 94/10317 | 5/1994 |

OTHER PUBLICATIONS

Mononen et al. Carbohydr. Res. 112: 165–170, 1983.*
Mononen et al. Carbohydr. Res. 104: 1–9, 1983.*
Sood et al. In: Abstracts of XIIIth International Carbohydrate Symposium, Paris, pp. 370, abstract BO37, Jul., 1992.*
Lindberg et al. Adv. Carbohydr. Chem. Biochem. 31: 185–239, 1975.*
Bayard et al. Carbohydr. Res. 46: 75–86, 1976.*
Jennings et al. In: Neoglycoconjugates: Preparation and Applications, YC Lee et al. (Ed), Academic Press, London, pp. 325–371, 1994.*
Paoletti et al. J. Biol. Chem. 265: 18278–18283 (A), 1990.*
Kasper et al. Vaccines 94, Cold Spring Harbor Laboratory Press, pp. 113–117, 1994.*
Paoleti et al. J. Clin. Invest. 89: 203–209 (B), 1992.*
Wessels et al. J. Biol. Chem. 66: 6714–6719, 1991.*
Madoff et al. J. Clin. Invest. 94: 286–292, abstract, 1994.*
Abstract of Grant No. 5R01AI30628–02, "Prevention of perinatal group B streptococcal infections (human, mice, rabbits)", Kasper D.L., Principal Investigator, Dialog File 265/266, Fed. Research in Progress, printout of Jan. 26, 1993 for fiscal year 1992.

(List continued on next page.)

Primary Examiner—S. Devi
(74) Attorney, Agent, or Firm—Morgan & Finnegan, L.L.P.

(57) ABSTRACT

The process for depolymerizing Group B Types II and III Streptococcal Polysaccharide is disclosed which results in polysaccharide fragments having a reducing end suitable for conjugating to protein. Conjugate molecules, vaccines and their use to immunize mammals including humans are also disclosed.

16 Claims, 6 Drawing Sheets

OTHER PUBLICATIONS

Abstract of Grant No. 2R37A23339–08, "Immunochemistry of Group B streptococcus polysaccharides (human, mice, rabbits)", Kasper, D.L., Principal Investigator, Dialog File 265/266, Fed. Research in Progress, printout of Jan. 26, 1993 for fiscal year 1992.

Attachment A (Work Statement) form Request for Proposal No. NIH–NIAID–DMID–92–13, issued by the Department of Health and Human Services for the National Institutes of Health on Jan. 21, 1992, entitled, "Prevention of Group B Streptococcal Infections in Neonatal and Infant Populations".

Baker, C.J., "Immunization to Prevent Group B Streptococcal Disease: Victories and Vexations", *Journal of Infectious Disease*, vol. 161, No. 5, pp. 917–921, May 1990.

Bittle, J.L., et al. "Vaccines Produced by Conventional Means to Control Major Infectious Diseases of Man and Animals", *Adv. Vet. Sci. Comp. Med.*, vol. 33, pp. 1–63, Feb. 1989.

Coleman, R.T., et al. "Prevention of Neonatal Group B Streptococcal Infections: Advances in Maternal Vaccine Development", *Obst. Gynec.*, vol. 80, No. 2, pp. 301–309, Aug. 1992.

Dick and Beurret (1989) "Glycoconjugates of Bacterial Carbohydrate Antigens—A Survey and Consideration of Design and Preparation Factors" Conjugate Vaccines) In *Contrib. Microbiol. Immunol.* (Cruse, JM and Lewis, RE. Tr. (eds.) Basel Karger vol. 10:48:114.

Dintzis, "Rational Design of Conjugate Vaccines", *Pediatric Research*, vol. 32, No. 4, pp. 376–385, Oct. 1992.

Feldman, et al. "The immune response to the group B streptococcus", *Reviews in Medical Microbiology*, vol. 3, No. 1, Jan. 1992, pp. 52–58.

Givner, et al. "Pooled Human IgH hyperimmune for type III Group B Streptococci: Evaluation against multiple strains in vitro and in experimental diseases", *J. Infectious Diseases*, vol. 163, pp. 1141–1145, May 1991.

Insel, R.A., "Maternal Immunization of Prevent Neonatal Infections", *New England Journal of Medicine*, vol. 319, No. 18, pp. 1219–1220, Nov. 1988.

Lerner, R.A., et al. "The Development of Synthetic Vaccines", *The Biology of Immunologic Disease*, Dixon, F.J., et al., eds., Sinauer Associates: Sunderland, MA, pp. 331–338, 1983.

Madoff, L.C., et al. "Protection of Neonatal Mice from Group B Streptococcal Infection by Maternal Immunization with Beta C Protein", *Infect. Immun.*, vol. 60, No. 12, pp. 4989–4994, Dec. 1992.

Paoletti, L.C., et al. "Group B Streptococcus Type III Glycoconjugate Vaccines", *Trends in Glycosci. Glycotech.*, vol. 4, No. 17, pp. 269–278, May 1992.

Pappenheimer, et al. (1972) "An Immunological Study of the Diptheria Toxin Molecule", *Immunochemistry*, vol. 9, pp. 891–906.

Sarvamangala et al. *Proc. Natl. Acad. Sci.* 88:7175–7179, 1991.

Sood et al. In: Abstracts of XIIth International Carbohydrate Symposium, Paris, pp. 370, abstract BO37, 1992.

Ward et al., "Haemophilus Influenza *Vaccines*" in Vaccines, Plotkin et al eds. W.B. Saunders Co., Philadelphia, 1988 p. 300–330.

Wilkinson, H.W., et al. "Type–Specific Antigens of Group B Type Ic Streptococci", *Infect. Immun.*, vol. 4, No. 5, Nov. 1971, pp. 596–604.

Wessels, et al. "Immunogenicity and Protective Activity in Animals of a Type V Group B Streptococcal Polysaccharide–Tetanus Toxoid Conjugate Vaccine", The Journal of Infectious Diseases, vol. 171, 1995, pp. 879–884.

Paoletti, et al. "Group B Streptococcus Type II Polysaccharide–Tetanus Toxic Conjugate Vaccine", Infection and Immunity, vol. 60, No. 10, Oct. 1992, pp. 4009–4014.

Rodewald, et al. "Neonatal Mouse Model of Group B Streptococcal Infection", The Journal of Infectious Diseases, vol. 166, 1992, pp. 635–639.

Lagergard, et al. "Synthesis and Immunological Properties of Conjugates Composed of Group B Streptococcus Type III Capsular Polysaccharide Covalently Bound to Tetanus Toxoid", Infection and Immunity, Mar. 1990, vol. 58, No. 3, pp. 687–694.

Heiman, et al. "The Opsonic Antibody Response of Female Rats to Type III Group B Streptococcal Immunization: a Model for Maternal Immunity", Veterinary Immunology and Immunopathy, vol. 24, 1990, pp. 79–89.

Roy, et al. "Efficient Synthesis of $\alpha$(2–8)–Linked N–Acetyl and N–Glycolylyneuraminic Acid Disaccharides from Colominic Acid", Journal of Glycoconjugate, vol. 7, 1990, pp. 3–12.

Wessels, et al. "Isolation and Characterization of Type IV Group B Streptococcus Capsular Polysaccharide", Infection and Immunity, vol. 57, No. 4, Apr. 1989, pp. 1089–1094.

Reuter, et al. "A Detailed Study of the Periodate Oxidation of Sialic Acids in Glycoproteins", The Journal of Glycoconjugate, vol. 6, 1989, pp. 35–44.

Baker, et al. "Immunization of Pregnant Women with a Polysaccharide Vaccine of Group B Streptococcus", The New England Journal of Medicine, vol. 319, No. 18, Nov. 3, 1988, pp. 1180–1185.

Wessels, et al. "Structure and Immunochemistry of an Oligosaccharide Repeating Unit of the Capsular Polysaccharide of Type III Group B Streptococcus", The Journal of Biological Chemistry, vol. 262, No. 17, Jun. 15, 1987, pp. 8262–8267.

Baker, et al. "Group B Streptococcal Vaccines", Reviews of Infectious Diseases, vol. 7, No. 4, Jul.–Aug. 1985, pp. 458–467.

Facklam, et al. "Streptococci and Aerococci", Manual of Clinical Biology, Fourth Edition, 1985, Chapter 16, pp. 154–175.

Kasper, et al. "Immunochemical Analysis and Immunogenicity of the Type II Group B Streptococcal Capsular Polysaccharide", J. Clin. Invest., vol. 72, Jul. 1983, pp. 260–269.

Jennings, et al. "Structural Determination of the Capsular Polysaccharide Antigen of Type II Group B Streptococcus", The Journal of Biological Chemistry, Feb. 10, 1983, vol. 258, pp. 1793–1798.

Jennings "Capsular Polysaccharides as Human Vaccines", Advances in Carbohydrate Chemistry and Biochemistry, Academic Press, vol. 41, 1983, pp. 155–208.

Jennings, et al. "Immunochemistry of Group A, B, and C and Meningococcal Polysaccharide–Tetanus Toxoid Conjugates", The Journal of Immunology, vol. 127, No. 3, Sep. 1981, pp. 1011–1018.

Jennings, et al. "Conformational Aspects Critical to the Immunospecificity of the Type III Group B Streptococcal Polysaccharide", Biochemistry, vol. 20, No. 16, Aug. 4, 1981, pp. 4511–4518.

Shaklee, et al., Biochem. J., 1986, pp. 235:225–236.

Bienkowski, et al., J Biol.Chem., 1985, pp. 260:356–365.
Porter, W. H., Anal. Biochem., 1975, pp. 63:27–43.
Wessels, et al. "Structure and Immunochemistry of an Oligosaccharide Repeating Unit of the Capsular Polysaccharide of Type III Group B Streptococcus", The Journal of Biological Chemistry, vol. 262, No. 17, Jun. 15, 1987, pp. 8262–8267.

* cited by examiner

ANTIGENIC GROUP B STREPTOCOCCUS TYPE II AND TYPE III POLYSACCHARIDE FRAGMENTS HAVING A 2, 5-ANHYDRO-D-MANNOSE TERMINAL STRUCTURE AND CONJUGATE VACCINE THEREOF

This is a divisional of co-pending application Ser. No. 08/481,883 filed Jun. 7, 1995, now co-pendimg.

FIELD OF THE INVENTION

This invention relates to antigenic capsular polysaccharide fragments useful for conjugating to a protein to create immunogens which elicit protective antibodies. More specifically, the invention relates to Group B Streptococcus capsular polysaccharides (GBS CP) with analyzable reducing-end groups, their preparation, and their use to make conjugate vaccines.

BACKGROUND OF THE INVENTION

GBS bacteria are a recognized etiological agent for bacteremia and/or meningitis in infants, and for infections in adults. Baker, "Group B Streptococcal Infections" in *Advances in Internal Medicine*, 25:475–500 (1980). Accordingly, it is important to develop rapid and definitive assays for diagnosis of GBS infection, and methods of generating protection against GBS, particularly in infants and compromised individuals.

The capsular polysaccharides from GBS bacteria are known to be important to GBS virulence and the development of protective immunity. See Kasper et al. U.S. Pat. No. 5,302,386. Moreover, the CP of recognized GBS types (I–V) are chemically related but antigenically distinct having repeating structures composed of galactose, glucose, N-acetyl glucosamine, and N-acetyl-neuraminic (sialic) acid.

Infants and young children have poor immunogenic response to polysaccharide antigens. These responses are characterized as being T cell independent and therefore are not associated with important attributes such as memory, isotype switching, or affinity maturation, which are necessary for conferring long term immunologic protection against subsequent infection. To circumvent this lack of an effective immunogenic response in infants and young children to polysaccharides, the art has developed means of converting the T cell independent response to T cell dependent response by covalently coupling polysaccharide bacterial antigens to a carrier protein to form a conjugate molecule. See, Jennings et al. U.S. Pat. No. 4,356,170, which is incorporated herein by reference.

Various procedures have been described in the art for conjugating capsular polysaccharides to proteins. For review, see *Contributions to Microbiology and Immunology*, vol 10, *Conjugate Vaccines*, volume editions J. M. Cruse and R. E. Lewis, Jr., 1989, which is incorporated herein by reference. In one method, polysaccharide is subjected to mild acid hydrolysis to produce reducing end groups capable of reacting with protein to form a covalent bond. Anderson, P. A., *Infect. Immun.*, 39:233–238 (1983). However, the terminal sugar groups which participate in conjugating to protein exist in equilibrium between a hemiacetal and aldehyde and therefore couple to protein with poor efficiency. To overcome the poor reactivity of the terminal reducing sugar, the art turned to mild oxidation to introduce stable aldehyde groups at terminal positions of polysaccharides used to conjugate to protein. Jennings et al. U.S. Pat. No. 4,356,170, supra.

Kasper et al. U.S. Pat. No. 5,302,386 and International application WO 94/06467, respectively relate to GBS type III and II conjugate vaccines, both of which are incorporated herein by reference. According to the 5,302,386 patent, endo-β-galactosidase is used to cleave the polysaccharide backbone to produce products suitable for conjugating to protein. Oxidation of at least two terminal sialic acid groups to produce cross-linked conjugates is described in the WO 94/06467 application.

Type III GBS capsular polysaccharides are composed of a backbone of repeating branched pentasaccharide units. Jennings et al., *Canadian J. Biochem.*, 58:112–120 (1980). One study of type III GBS polysaccharides reports that the natural immunodeterminant site is located at the side chain-backbone junction. Jennings et al., *Biochemistry*, 20:4511–4518 (1980). The presence of the side chain terminal N-acetyl-neuraminic acid residues reportedly was critical for immunodeterminant expression.

Prior methods of depolymerizing GBS II or III polysaccharides rely on either costly enzymatic methods or on acid hydrolysis which may alter the antigenicity of the CP due to removal of the labile terminal sialic acid groups. Accordingly, there is a need for relatively inexpensive and mild chemical procedures which are effective for depolymerizing GBS type II and III CP in a manner which results in fragments which are useful for producing CP-protein conjugate vaccines.

SUMMARY OF THE INVENTION

This invention relates to a method of depolymerizing Group B Streptococcus type II (GBS-II) and type III (GBS-III) capsular polysaccharides (CP) by deaminative cleavage to generate products terminating with a 2,5-anhydro-D-mannose structure. According to this invention, the GBS-II CP and GBS-III CP are treated with sodium hydroxide and a nitrosation reagent such as sodium nitrite to depolymerize the GBS polysaccharides to produce fragments having a terminal aldehyde group located at the end of the polysaccharide backbone. The resulting CP fragments are antigenic and are also useful for conjugating to protein to produce immunogens which are effective for eliciting protective immune responses in mammals including neonates.

Another embodiment of this invention therefore is a method of making a conjugate molecule for use as a vaccine. The method comprises subjecting GBS-II or GBS-III CP to treatment by base and a diazonium salt forming reagent to form a fragment terminating with a 2,5-anhydro-D-mannose residue. The 2,5-anhydro-D-mannose terminating fragment is then combined with a protein and subjected to reductive amination to form the conjugate molecules of the invention. Accordingly, another aspect of this invention are GBS-II and GBS-III CP conjugate molecules comprising GBS-II or GBS-III CP fragments linked to protein through a terminal 2,5-anhydro-D-mannose. Because the process of depolymerizing the GBS type II and type III polysaccharides generates fragments having a single reactive site at the terminal end of the backbone, this invention provides a means of producing conjugate molecules wherein each GBS type II or III polysaccharide chain is bound to a single protein, each by a secondary amine through the terminal reducing sugar.

The conjugates of this invention are useful as active vaccines for immunizing individuals against GBS-II and GBS-III bacterial infection. Also provided by this invention are multivalent vaccines comprising polysaccharides derived from different serotypes or species of bacteria.

In addition, this invention encompasses immune serum or antibodies raised in response to immunization with the conjugate molecules of this invention and which are useful as reagents for detecting the presence of GBS type II or III bacteria or as vaccines for conferring passive immunity.

Another embodiment of this invention are methods and compositions useful for separating and/or detecting GBS type II or type III antibodies. According to one mode of practicing this embodiment, the polysaccharide fragments prepared according to this invention are immobilized onto a solid support. By combining a source of antibody such as serum, with the polysaccharide fragment bound to the solid support, the antibody which bonds to the polysaccharide fragment may be detected by standard immunoassay techniques or separated from the starting material or serum.

An object of this invention is to provide methods for fragmenting GBS type II and III polysaccharides to produce fragments useful producing conjugate molecules. Another object of this invention is to produce GBS type II and type III polysaccharide molecules which are useful as vaccines to protect against infection and as immunoreagents.

DETAILED DESCRIPTION OF THE INVENTION

Figure 1:
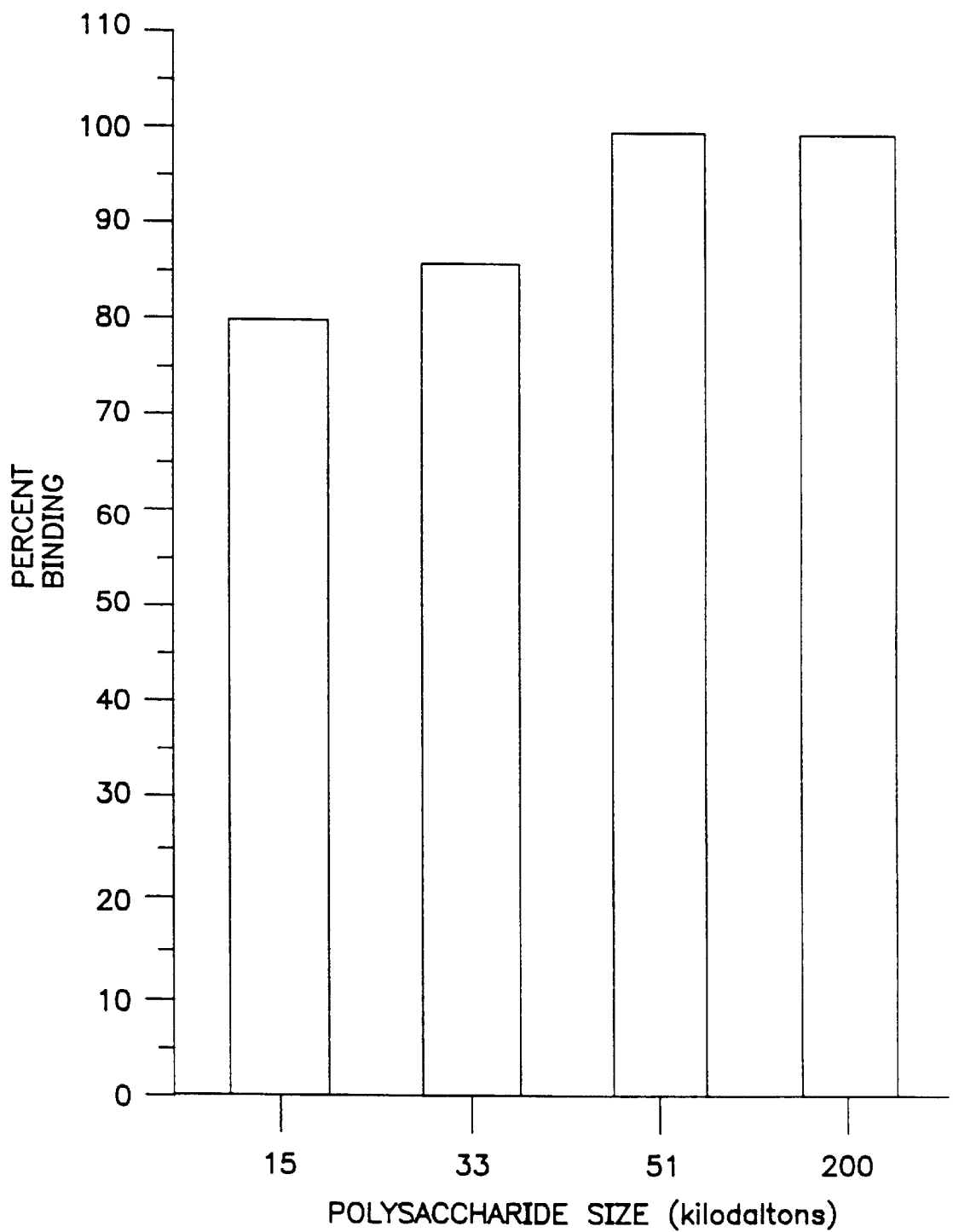
FIG. 1. Direct binding of rabbit anti-type II specific polysaccharide antibody to type-II-fragment polysaccharide-tetanus toxoid conjugates (with fragments of average molecular weights 15, 33 and 51 kilodaltons) compared with the binding to the type II native polysaccharide (200 kilodaltons)-tetanus toxoid conjugate taken as 100% binding reference.

This invention relates to Group B Streptococcus type II and type III antigen polysaccharide-fragments having the following 2,5-anhydro-D-mannose reducing-end structure:

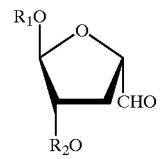

wherein $R_1$ is H and $R_2$ is a sialylated heptasaccharide repeating-unit of formula

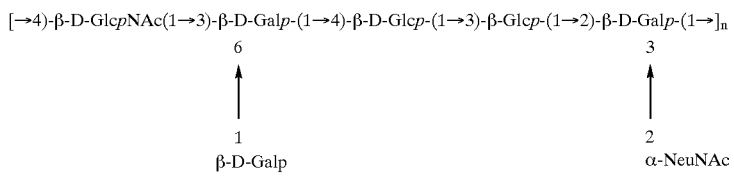

wherein n is about 5 to about 50 for GBS type II; and wherein $R_1$ is a sialylated pentasaccharide repeating-unit of formula

[→4)-β-D-Glc$p$(1→6)-β-D-Glc$p$NAc-(1→3)-β-D-Gal$p$(1→]$_n$
4
1
β-D-Gal$p$
3
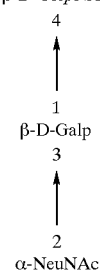
2
α-NeuNAc wherein n is about 5 to 50 and $R_2$ is disaccharide αNeuAc (2-3)β-D-Galp1- for GBS type III.

These fragments are produced according to this invention by depolymerizing larger molecular weight GBS type II and III polysaccharides having the structures shown below:

TYPE II

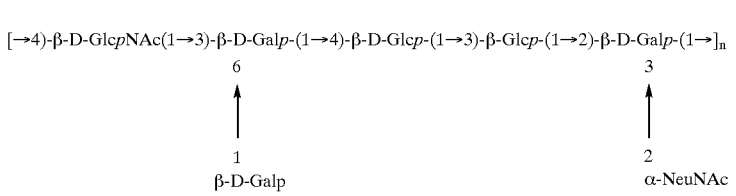

wherein n for the native polysaccharide is about 200; or the repeating unit for GBS type III

TYPE III

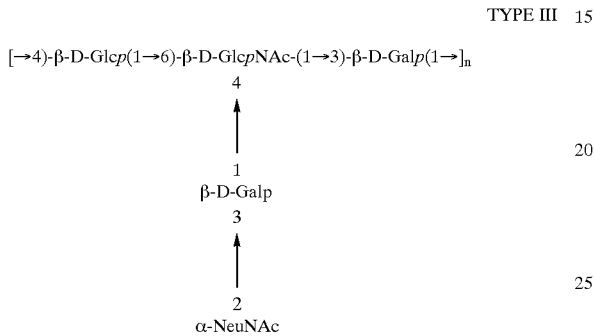

wherein n for the native polysaccharide is about 100.

As used herein, the term Group B Streptococcus or (GBS) bacteria has the same meaning as understood by those in the art, particularly with reference to Lancefield, *J. Exp. Med.*, 108:329–341 (1938) and subsequent work further characterizing Group B serotypes, e.g. Russell-Jones, *J. Exper. Med.*, 160:1476 (1984), to specifically include bacteria taxonomically designated *Streptococcus agalactiae*.

The process of this invention for fragmenting the GBS type II and III capsular polysaccharide to produce the novel fragments of the invention uses mild non-denaturing conditions to obtain GBS type II and GBS type III polysaccharide fragments resulting from chemical depolymerization. These fragments may be obtained in high yield making this process economical for large scale production of vaccines.

GBS type II and III CP are depolymerized according to the method of this invention as follows. The backbone 2-deoxy-2N-acetamido-β-D glucopyranosyl residues in the type II and type III GBS CP (Formula I) is partially de-N-acetylated with mild base in an aqueous solution. Examples of bases which are suitable for use in the process of this invention include, but are not limited to aqueous alkali metal hydroxide solutions for example, sodium hydroxide or potassium hydroxide, or other bases such as ammonium hydroxide, hydrazine, sodium carbonate and sodium bicarbonate. Following base treatment, the resulting glucosamine residue (Formula II) is then susceptible to nitrosation using an appropriate reagent such as sodium nitrite or nitrous acid, for example, to form an unstable N-nitroso derivative (Formula III). Rearrangement due to nucleophilic attack by the ring oxygen on carbon 2, results in ring contraction and cleavage of the adjacent glycosidic linkage. (Formula IV). This reaction has been used to study the structure of heparin and various glycosaminoglycans. Barnett U.S. Pat. No. 4,438,261, which is incorporated herein by reference.

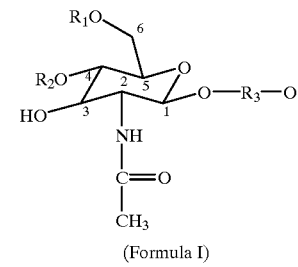

(Formula I)

1) Base

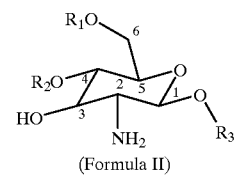

(Formula II)

2) $NaNO_2$

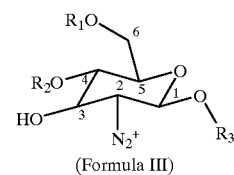

(Formula III)

Rearrangement

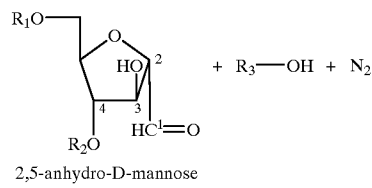

2,5-anhydro-D-mannose
(Formula IV)

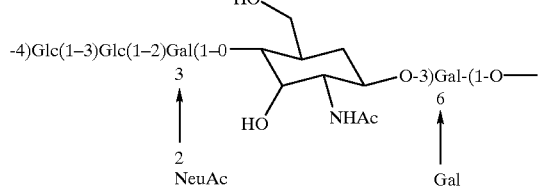

1) Base
2) $NaNO_2$

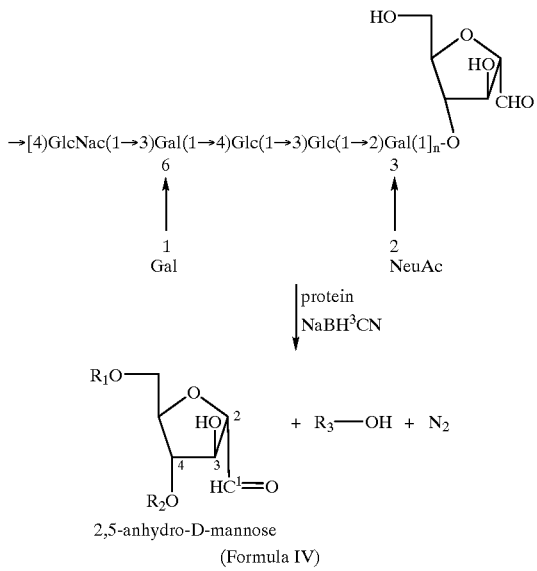

2,5-anhydro-D-mannose
(Formula IV)

The aldehyde group in the resulting 2,5-anhydro-D-mannose (Formula IV) residue formed at the reducing end of the polysaccharide fragment can be used directly, without further chemical manipulation (e.g. use of a spacer arm), for linking through reductive amination to an amino group containing polymer, preferably a protein.

More specifically, to carry out the depolymerisation of the GBS polysaccharides according to the invention, the reaction is carried out in a convenient size vessel in an aqueous solution. To begin the reaction, an appropriate amount of polysaccharide in an aqueous solution is treated with a base to partially de-N-acetylate the backbone glucopyranosyl residue. Briefly, the reaction can be carried out in a basic aqueous medium at elevated temperatures, for example about 50° C. to 110° C., and at a pH of about 13 to 14. The amount of base be optimized empirically. Preferably the ratio of base to N-acetyl groups is between about 10 to 50 meq. More preferably the ratio is about 20–25 meq. The rate and extent of reaction may be optimized by adjusting the base concentration, reaction temperature or time of reaction. The extent of de-N-acetylation may be monitored by ¹H-NMR.

To achieve fragments of between about 5 to 60 kDa, the degree of de-N-acetylation should be between about 20 to about 2 percent of the total number of available sites. To stop the deacetylation reaction, the reaction may be cooled, i.e., chilled on ice, or acidified to about pH 4. Acidification must be done carefully to avoid hydrolysis of remaining sialic acid groups.

The nitrosation reaction to form the aldehyde is then achieved by addition of sodium nitrite, or other suitable reagent, such as dilute nitrous acid, to the de-N-acetylated polysaccharide. The nitrosation reagent such as sodium nitrite preferably is added in molar excess compared to the moles of de-N-acetylated groups. Reaction of the polysaccharide with the nitrosation reagent is carried out at cold temperatures, for example about 4° C. with stirring, for approximately 2 hours or until completion. The extent of the reaction may be monitored by assaying for the presence of aldehyde groups. Over the course of the reaction, the concentration of aldehyde groups should increase until a plateau is reached. Termination of the reaction may be accomplished by dilution of the reaction and by raising the pH to about 7 with dilute base such as NaOH. Removal of excess reagents may be accomplished by dialysis using standard procedures.

After completion of the reaction, polysaccharide fragments having a terminal aldehydic group at the end of the backbone may be sized and collected using standard chromatography procedures. Preferred sizes for conjugation to protein are between 5 kDa and 50 kDa for the GBS type II polysaccharide and between about 5 kDa and 50 kDa for the GBS type III polysaccharide. More preferred sizes are between 5 and 20 kDa for GBS type II and between 10 and 50 kDa for GBS type III polysaccharides. The sized fragments may be used for conjugation reactions using standard reductive amination procedures previously described (See for example U.S. Pat. No. 4,356,170 and International application WO 94/06467) or may be stored for later use.

Deaminative cleavage and conjugation applied to GBS type II may be accomplished according to the invention as follows:

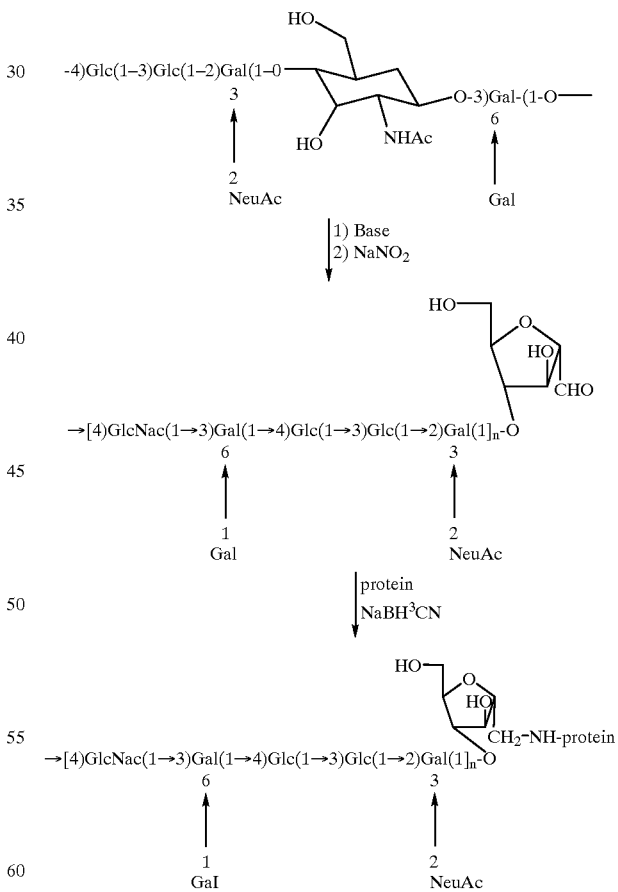

The process of depolymerization of the type III polysaccharide by deaminative cleavage generating antigenic type III fragments which can be coupled directly by reductive amination to a carrier protein is illustrated below:

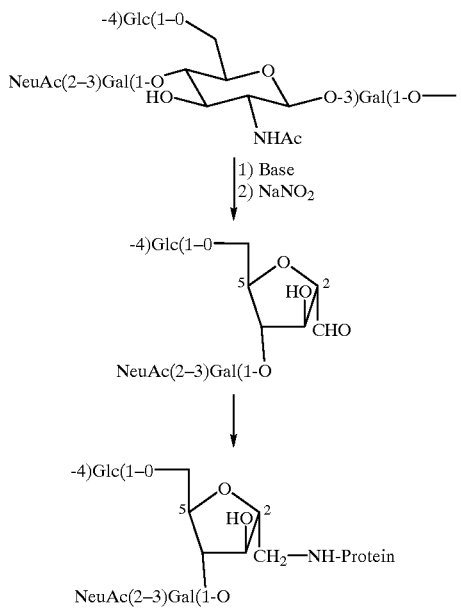

The protein component of the conjugate molecules of the invention may be any physiologically tolerated protein or polypeptide of sufficient length to evoke a T cell dependent response. Examples of such proteins include, but are not limited to bacterial proteins, or polypeptides, including tetanus toxin or toxoid, cross reactive materials such as $CRM_{197}$, a recombinant non IgA binding protein of the β-C antigen of type Ia/Ib Group B streptococcus, and recombinant class 3 Outer Membrane Protein and (OMP) from *Neisseria Meninqitides*.

The molar ratio of polysaccharide to protein in the conjugate molecules of the invention is preferably between about 1 mole to about 10 moles polysaccharide per mole protein. More preferably the ratio is between 3 and 10 polysaccharide fragments per mole of protein. Variations in protein/polysaccharide ratio may be achieved by adjusting the ratio of the starting components in the conjugation reaction.

In addition to providing conjugate molecules comprising GBS type II or III polysaccharides conjugated to protein, this invention also contemplates multivalent: conjugates and their vaccines wherein different types of polysaccharides are conjugated to a single protein. For example, the polysaccharides of GBS types I, II, III, IV or V may be bound to protein in various combinations, as well as polysaccharides derived from other bacteria such as, for example, *Haemophilus influenzae* type b, or meningococcus types A, B or C as well. A preferred combination would be polysaccharides of GBS type II and III.

The conjugate molecules prepared according to this invention typically comprise a protein to which is bound at least one GBS type II or III polysaccharide fragment through a single binding site at the terminal end of the backbone of the polysaccharide fragment. Thus, this invention provides the ability, if desired, to produce GBS type II or III conjugate molecules wherein the polysaccharide component, except for one end, is unobscured by protein. Other methods of conjugating GBS type II and III polysaccharides to protein through the terminal sialic acids of the branches may result in crosslinking, and attachment of polysaccharide to protein at a plurality of sites. This invention also contemplates conjugate molecules which may be made using a combination of methods. For example, conjugates synthesized according to the invention by producing a single reactive 2,5-annhydro-D-mannose terminal group may be further reacted with polysaccharides which have been activated at multiple sites.

The process of preparing vaccines according to this invention provides useful vaccines which are important for providing protection against GBS type II and III infection in mammals, and in particular females of child bearing age, neonates, immunocompromised adults, and children who are at risk for GBS infection. These vaccines are expected to be especially useful for administration to pregnant women as a means of evoking an immunogenic response in the fetus prior to birth.

Vaccines are administered in amounts sufficient to provoke an immunogenic response. Typically a dose of between about 1 and 50 μg of polysaccharide for generating such a response. Dosages may be adjusted based on the size, weight or age of the individual receiving the vaccine. The antibody response in an individual can be monitored by assaying for antibody titer or bactericidal activity and boosted if necessary to enhance the response.

Vaccines may comprise standard carriers, buffers or preservatives known to those in the art which are suitable for vaccines. In addition, adjuvants such as alum or stearyl tyrosine may also be included in the formulation to enhance the immunogenic response.

The polysaccharide fragments prepared according to this invention are also useful for preparing various immuno reagents for use in immunoassays and separations of GBS type II or III antibodies. For example, for immunoassays the polysaccharide fragments may be immobilized either directly or through a protein linker as in the conjugates of this invention to a solid support. The solid support can then be used in various immunoassay systems known to those in the art including radioimmuno and ELISA assays for detecting the presence of antibodies to GBS type II or III bacteria. Such assays may be used for diagnosing the presence of infection in individuals by assaying for the presence of GBS type II or III antibodies in serum.

For use in separation chemistry, the polysaccharide fragments may be immobilized to a solid support to prepare an affinity column. In a preferred embodiment, the polysaccharide fragment is first conjugated to protein according to the method of this invention and the resultant conjugate is then coupled to a support matrix. Methods of coupling protein to affinity columns are known to those skilled in the art. Common supports for affinity columns are prepared from agarose and are commercially available, e.g. activated Sepharose (Pharmacia). Such affinity columns may then be used for separating GBS type II or III antibodies from sources such as serum. Antibody may then be separated from serum by combining the immobilized polysaccharide fragments with serum suspected of containing GBS type II or III antibodies under conditions which allow for antibodies to bind to immobilized fragments. The bound antibody may then either be detected using conventional assay techniques, or separated and recovered from the polysaccharide fragment following separation of the remaining serum components from the immobilized support.

The invention will now be described with reference to the following, non-limiting examples.

EXAMPLES

Example 1

Base Depolymerization and Sodium Nitrite Mediated Ring Contraction To Produce GBS Type II And III 2,5-anhydro-D-Mannose Terminated Fragments GBS Type II Native type II GBS CP (75 mg) of average molecular weight about 200,000 was dissolved in 3 ml of 0.5 N NaOH and the solution was then divided in 3 parts (1 ml each). The samples (S1–S3) were heated at 70° C. for 60, 90 and 180 min respectively, then chilled in an ice-water bath. 125 mcL of glacial acetic acid was added to each sample to bring their pH to 4. Following addition of 200 mcL of 5% (w/v) $NaNO_2$ the samples were kept under stirring at 4° C. for 2 hrs. S1–S3 samples were then diluted to 5 ml with DI water and their pH adjusted to 7 with 0.5 N NaOH. Excess reagents were dialysed out by diafiltration with DI water through a DIAFLO ultrafiltration membrane (Amicon YM 10) and the solutions were lyophilized. Three type II polysaccharide fragments (II-1–II-3) were obtained.

GBS Type III

Native type III GBS PCP (125 mg) of average molecular weight about 100,000 was dissolved in 5 ml of 0.5 N NaOH and the solution was then divided in 5 parts (1 ml each). The samples (S1–S5) were heated at 70° C. for 60, 90, 120, 180 and 240 min respectively, then chilled in an ice-water bath. 125 mcL of glacial acetic acid was added to each sample to bring their pH to 4. Following addition of 200 mcL of 5% (w/v) $NaNO_2$ the samples were kept under stirring at 4° C. for 3 hrs. S1–S5 samples were then diluted to 5 ml with DI water and their pH adjusted to 7 with 0.5 N NaOH. Excess reagents were dialysed out by diafiltration with DI water through a DIAFLO ultrafiltration membrane (Amicon YM 10) and the solutions were lyophilized. Five type III polysaccharide fragments (III-1–III-5) were obtained.

Sizing of CP Fragments

The average molecular weight (avMw)(of each fragment was estimated by HPLC using a SUPEROSE-12 size exclusion column (Pharmacia) with a dextran series (Pharmacia) of average molecular weight ranging from 10,000 to 2,000 daltons. Void volume (Vo) and total volume (Vt) were determined with Dextran 2,000 and sodium azide respectively. The average molecular weight (avMw) of each fragment determined by this method is as follows:

| Fragment | Kav (range) | AvMw Kilodaltons | (range) |
|---|---|---|---|
| II-1 | 0.23 (0.13–0.34) | 51 | (99–26) |
| II-2 | 0.30 (0.19–0.40) | 33 | (68–17) |
| II-3 | 0.43 (0.30–0.50) | 15 | (33–9) |
| III-1 | 0.21 (0.11–0.27) | 41 | (81–28) |
| III-2 | 0.26 (0.17–0.38) | 30 | (53–13) |
| III-3 | 0.29 (0.18–0.40) | 24 | (50–12) |
| III-4 | 0.37 (0.23–0.44) | 14 | (36–9) |
| III-5 | 0.41 (0.31–0.47) | 11 | (21–8) |

Physico-chemical Analysis of the Polysaccharide Fragments

The structural integrity of each fragment with respect to their parent native polysaccharide was established by high resolution one-dimensional H-NMR spectroscopy at 500 MHZ on a Bruker AM500 spectrometer. Comparison of the H-NMR spectra of the type II and type III fragments with those of their respective native polysaccharides indicated that no structural change had occurred during the chemical processes, and most importantly that terminal sialic acid residues had been, preserved during the nitrosation treatment.

Example 2

Conjugation of the Type II and Type III Polysaccharide Haptens to Tetanus Toxoid Tetanus toxoid (SSI, Denmark) was first purified to its monomeric form by gel filtration through a BIOGEL-A column (Biorad Laboratories). The tetanus toxoid monomer (TTm) thus obtained (150,000 Daltons) was solubilized in 0.2 M phosphate buffer, pH 7.5, at a concentration of 25 mg/ml and added to dried GBS type II (II-1 to II-3) or type III (III-1 to III-5) polysaccharides and recrystallized sodium cyanoborohydride $NaCNBH_3$ in the amounts shown below:

|  | PS (mg) | TTm (mg) | $NaCNBH_3$ (mg) | Final vol (ul) |
|---|---|---|---|---|
| II-1 | 10 | 4 | 8 | 200 |
| II-2 | 10 | 4 | 8 | 200 |
| II-3 | 11 | 4.5 | 9 | 220 |
| III-1 | 18 | 7.2 | 14 | 360 |
| III-2 | 10 | 4 | 8 | 200 |
| III-3 | 7.2 | 3 | 6 | 150 |
| III-4 | 6.4 | 2.5 | 5 | 130 |
| III-5 | 8 | 4 | 8 | 130 |

The reaction mixtures were then incubated at 37° C. for 4 days. The progress of the conjugation reaction was monitored by HPLC of small aliquots of the reaction mixtures analyzed on SUPEROSE-12 (Pharmacia). The conjugates were purified by molecular exclusion chromatography on a column of SUPERDEX G-200 (Pharmacia) using PBS containing 0.01% thimerosal as an eluant. Fractions eluting from the column were monitored by a Waters R403 differential refractometer and by UV spectroscopy at 280 nm. The fractions containing the conjugates were pooled sterilefiltered through a 0.22 μm Millipore membrane and analyzed, respectively, for their protein and sialic acid contents by the method of Bradford (Bradford, M. M., 1976. *Anal. Biochem.*, 72:248–254) and by the resorcinol assay. The average total amount of carbohydrate in each type II and type III individual conjugate molecule was calculated by taking the sialic acid content and multiplying them by a correction factor of 4 and 3.3 respectively based on the composition of their repeating-unit. The analyses for each individual conjugate are as shown in Table 1 below:

TABLE I

| Conjugate | AvMw PS chains | Protein (mcg/ml) | CHO (mcg/ml) | % CHO in conjugate | #PS chains |
|---|---|---|---|---|---|
| II-1-TT | 51,000 | 120 | 15 | 11 | 0.4 |
| II-2-TT | 33,000 | 140 | 42 | 23 | 1.4 |
| II-3-TT | 15,000 | 110 | 26 | 19 | 2.4 |
| III-1-TT | 41,000 | 190 | 70 | 27 | 1.2 |
| III-2-TT | 30,000 | 140 | 61 | 29 | 1.8 |
| III-3-TT | 24,000 | 100 | 39 | 28 | 2.0 |
| III-4-TT | 14,000 | 70 | 17 | 20 | 2.0 |
| III-5-TT | 11,000 | 80 | 21 | 21 | 3.0 |

The immunochemical specificity of rabbit polyclonal antibodies for the type II and type III polysaccharide-conjugates as compared to those observed for the native capsular polysaccharides epitopes was measured by ELISA and is reported in FIGS. 1 (GBS-type II) and 2 (GBS type III).

Example 3

Immunogenic Response of Female Mice To Immunization With GBS Type II and Type III— Tetanus Toxoid Conjugate Vaccines a. Immunizations Groups of 10 Swiss Webster female mice (4–6 weeks old) were immunized subcutaneously with 2 μg of either native type II or III polysaccharide or their corresponding Tetanus-toxoid conjugates. The vaccine were absorbed on aluminum hydroxide (Alhydrogel; Superfos, Denmark) at a concentration of 1 mg of elemental aluminum/ml of 10 mM PBS containing 0.01% thimerosal. Mice received the vaccine at days 0, 21 and 42 and finally were exsanguinated at day 52. Sera were collected and stored at 70° C.

b. ELISAs and opsonic activity of conjugate antisera

ELISAs: Microtiter plates (Nunc Polysorb ELISA plates) were sensitized by adding 100 μL of native type II or III polysaccharide-HSA conjugate (1 μg/ml) in PBS with 0.02% azide per well. The plates were incubated at 37° C. for one hour. The plates were washed with PBS containing 0.05% TWEEN 20 (PBS-T) and blocked with 0.5% BSA in PBS for one hour at r.t. The wells were then filled with 100 μL of serial two-fold dilutions in PBS-T of mice antiserum and the plates were incubated at r.t. for one hour. After washing with PBS-T, plates were filled with 100 μL of peroxidase labeled goat anti-mouse IgG(H+L) (Kirkegaard & Perry Laboratories) and then washed five times with PBS-T. Finally, 50 μL of TMB peroxidase substrate (Kirkegaard & Perry Laboratories) were added to each well and following incubation of the plates for 10 min. at r.t. the reaction was stopped by the addition of 50 μL of 1M $H_3PO_4$. The plates were read at 450 nm with a Molecular Device Amex microplate reader using 650 nm as a reference wavelength.

Type III polysaccharide-specific antibody titers of mice vaccinated with native type III polysaccharide or type III fragment polysaccharide-Tetanus toxoid conjugates as shown in Table II.

TABLE II

| Average MW of fragment | ELISA titer at day 52* | OP Titer+ |
|---|---|---|
| 13,000 | 2,500 | 405 |
| 18,000 | 2,500 | 610 |
| 26,000 | 3,000 | 1,050 |
| 34,000 | 3,000 | 520 |
| 48,000 | 12,000 | 2,600 |
| Native PS | <100 | <100 |

*Mean titer of serum pooled from 10 mice.
+Opsonophagocytic killing of pooled serum at day 52.

Type II polysaccharide-specific antibody titers of mice vaccinated with native type II polysaccharide or type II fragment polysaccharide-Tetanus toxoid conjugates is shown in Table III.

TABLE III

| Average MW of fragment | ELISA titer at day 52* | OP Titer+ |
|---|---|---|
| 15,000 | 123,000 | 9,300 |
| 33,000 | 15,000 | 1,400 |
| 51,000 | 2,600 | <500 |
| Native PS | <500 | <100 |

*Mean titer of serum pooled from 10 mice.
+Opsonophagocytic killing of pooled serum at day 52.

Opsonic Activity of Conjugate Antisera: The opsonic ability of mice antisera to the GPS type II or type III polysaccharide-fragment-tetanus toxoid conjugates was tested in an in vitro opsonophagocytic killing assay using the human promyelocytic leukemia HL-60 cell line (ATCC No. CCL 240). Briefly, 200 cfu of GBS type II strain 18RS21 cells or type III strain M781 cells were mixed in equal volume with serum antibodies and incubated under shaking 15 min. at 35° C. in a 5% $CO_2$ incubator. Baby rabbit complement and HL-60 cells ($5 \times 10^5$) cultured 5 days in the presence of 90 mM DMF were added to the mixture and incubated at 37° C. for 1 hour under shaking. Aliquots were removed for quantitative culture. Titers were determined by extrapolating the antibody dilution corresponding to fifty percent live bacteria.

c. ELISA binding experiments: Direct binding of rabbit anti-GBS type II or type III capsular polysaccharide specific antibodies (obtained from rabbits hyper-immunized with type III or type II GBS whole cells) to the various tetanus-toxoid conjugates was carried out: as follows:

Microtiter plates were sensitized with 100 μl of various sizes of the GBS type II or type III polysaccharide-tetanus-toxoid (TT) conjugates (1 μg/ml) in PBS containing 0.01% thimerosal per well. The plates were incubated at r.t. for one hour, processed as described above, and filled with 100 μl of serial two fold dilutions of rabbit antiserum diluted in PBS-T. The remaining ELISA steps are as described above except for the addition of the secondary peroxidase labeled goat anti-rabbit IgG (H&L) (Kirkegaard & Perry Laboratories).

Figure 2:
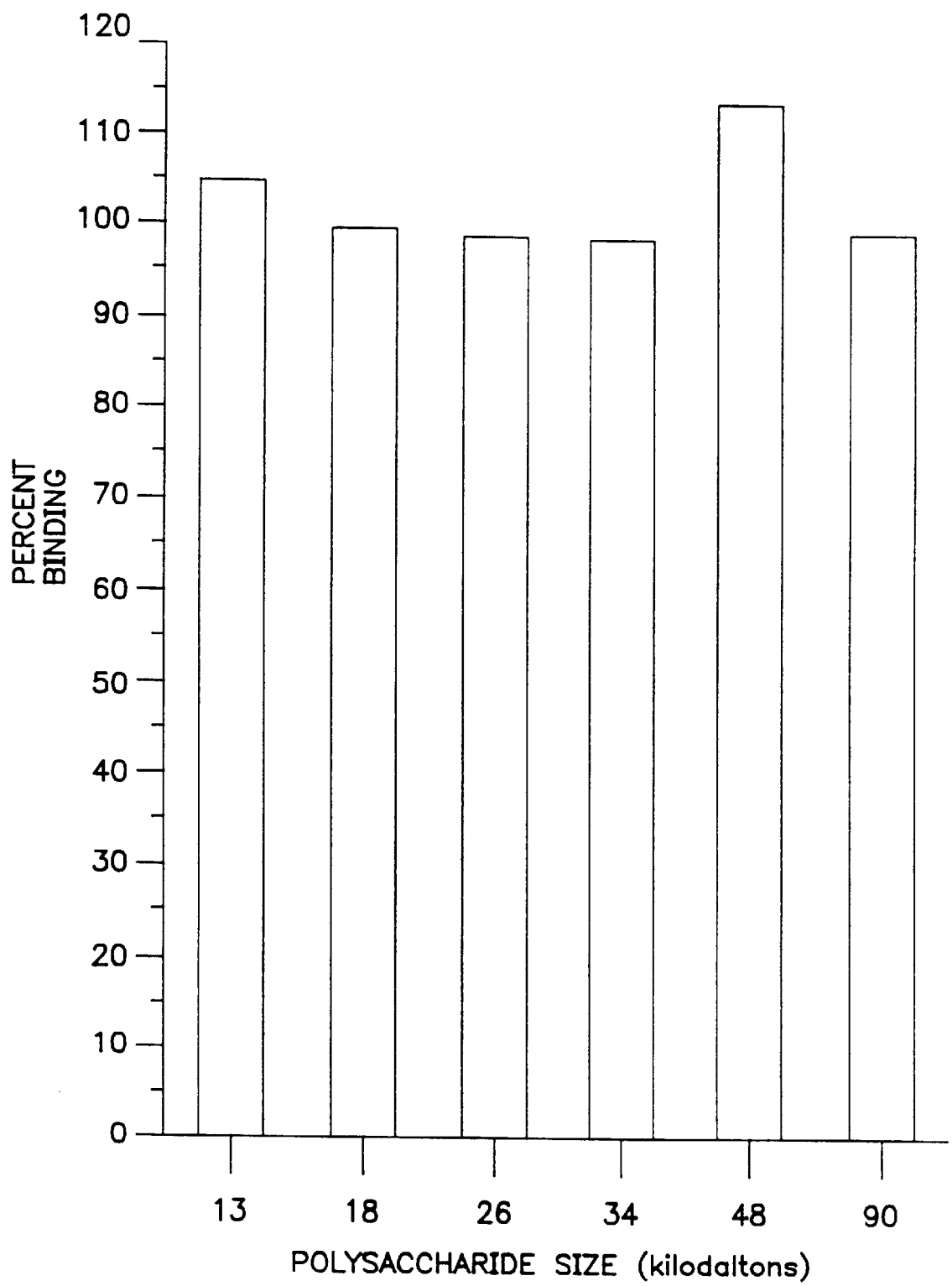
FIG. 2. Direct binding of rabbit anti-type III specific polysaccharide antibody to type III fragment polysaccharide-tetanus-toxoid conjugates (with fragments of average molecular weight 13, 18, 26, 34 and 48 kilodaltons) compared with the binding to the type III native polysaccharide (90 kilodaltons)-tetanus toxoid conjugate taken as 100% binding reference.
Figure 3:
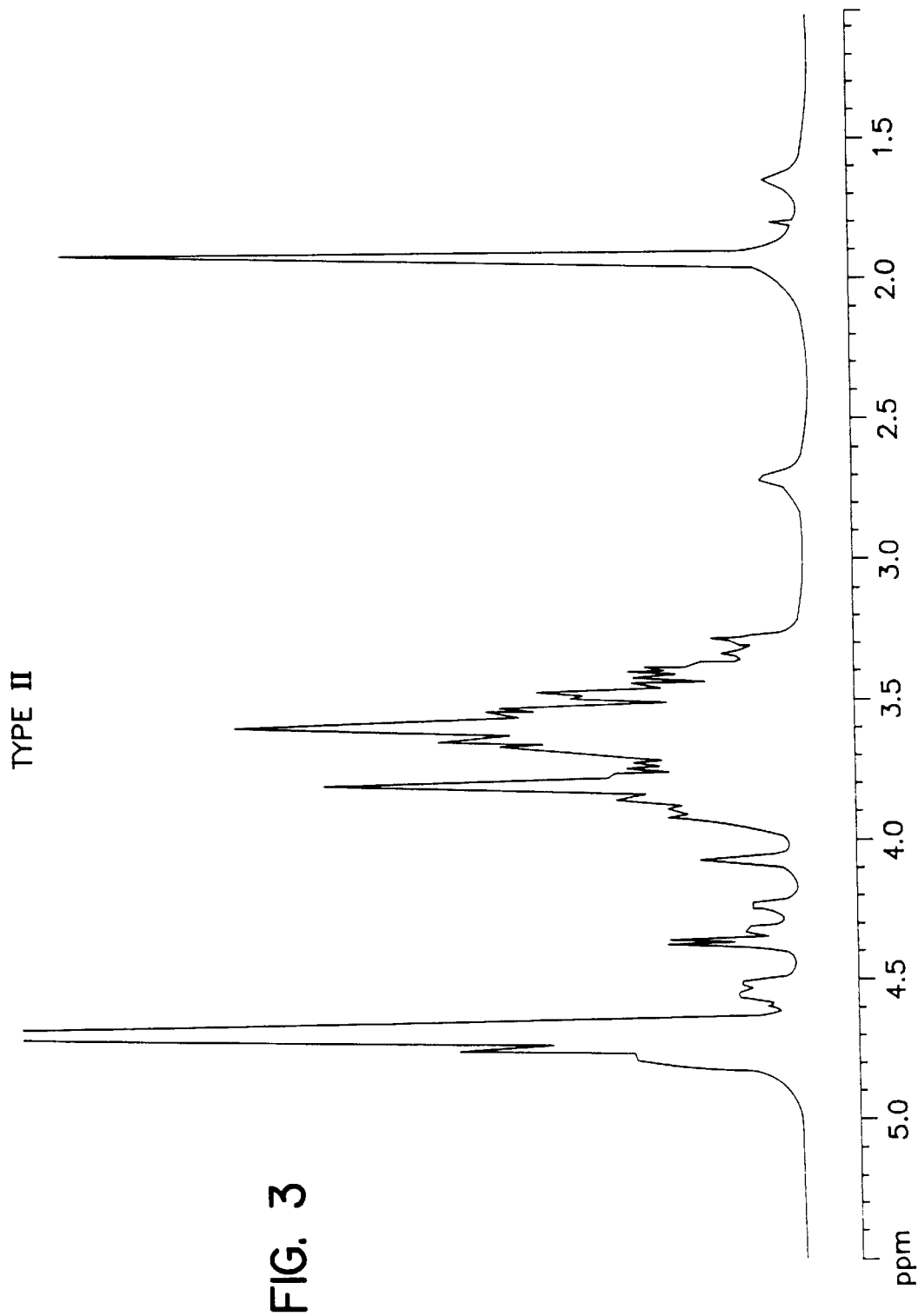
FIG. 3. H-NMR spectrum of native GBS type II polysaccharide having a molecular weight of approximately 200 kDa.
Figure 4:
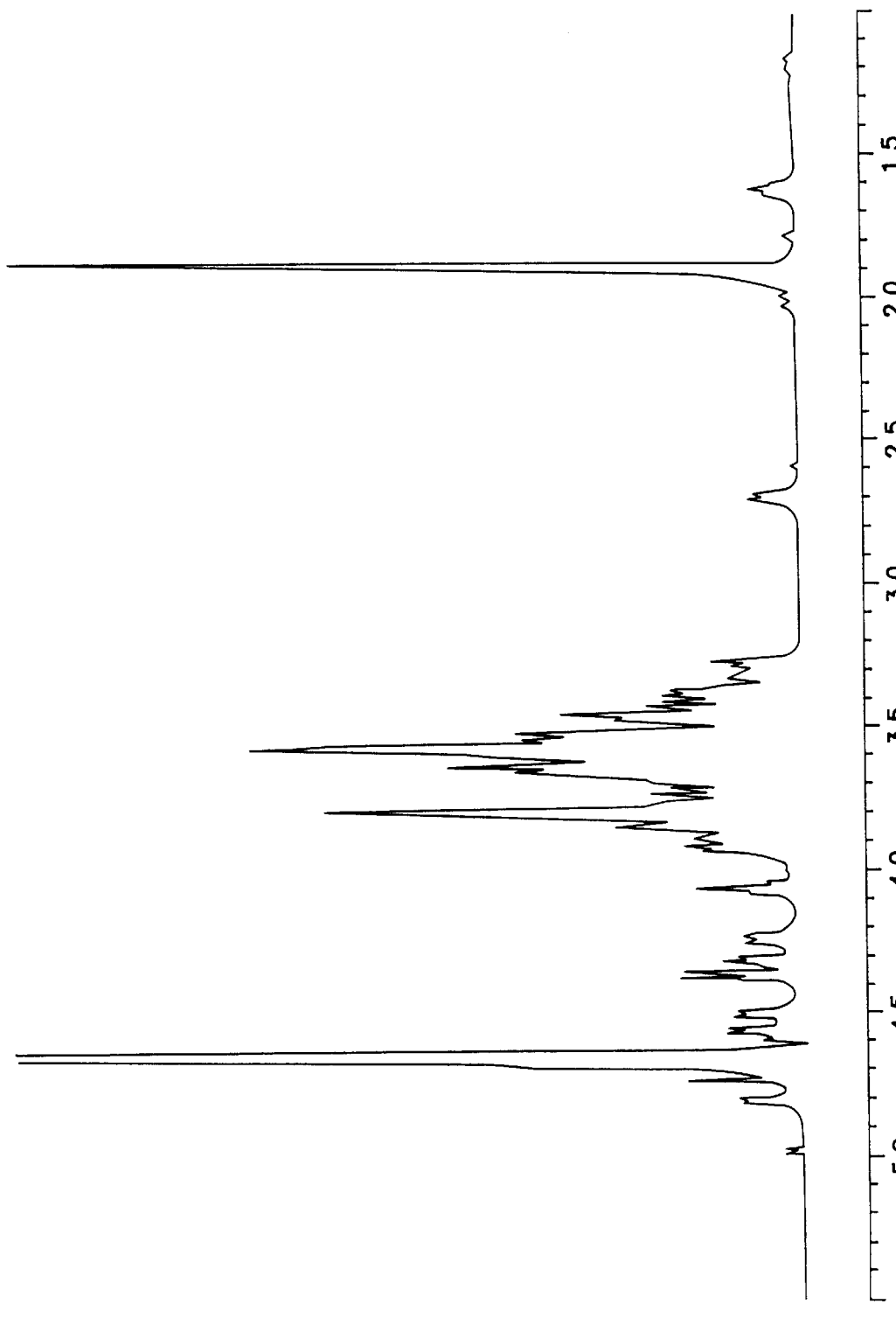
FIG. 4. H-NMR spectrum of GBS type II polysaccharide fragment having a molecular weight of approximately 12 kDa and showing the proton peaks associated with the 2,5-anhydro-D-mannose prepared according to the method of this invention.
Figure 5:
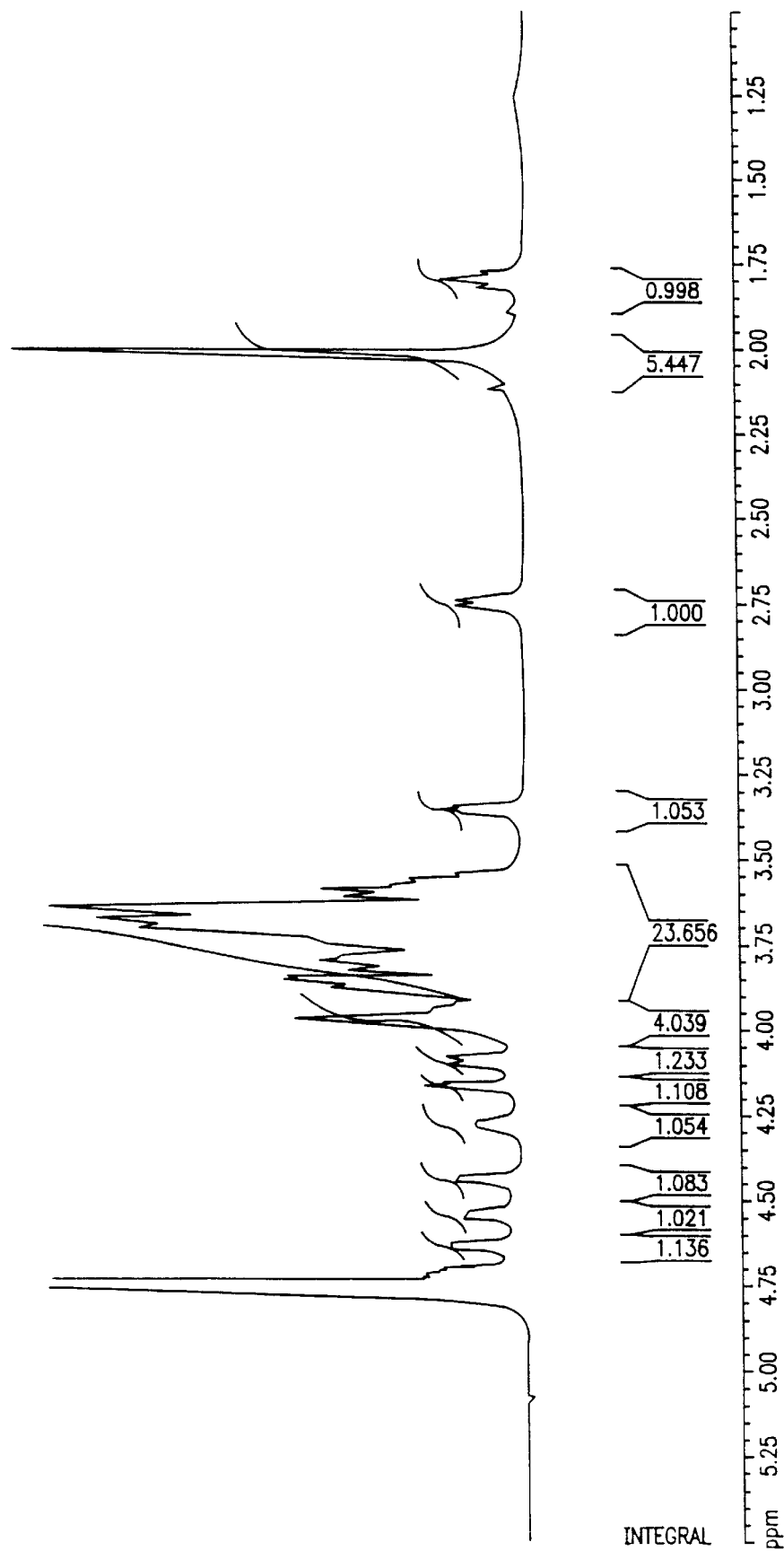
FIG. 5. H-NMR spectrum of native GBS type III polysaccharide having a molecular weight of approximately 100 kDa.
Figure 6:
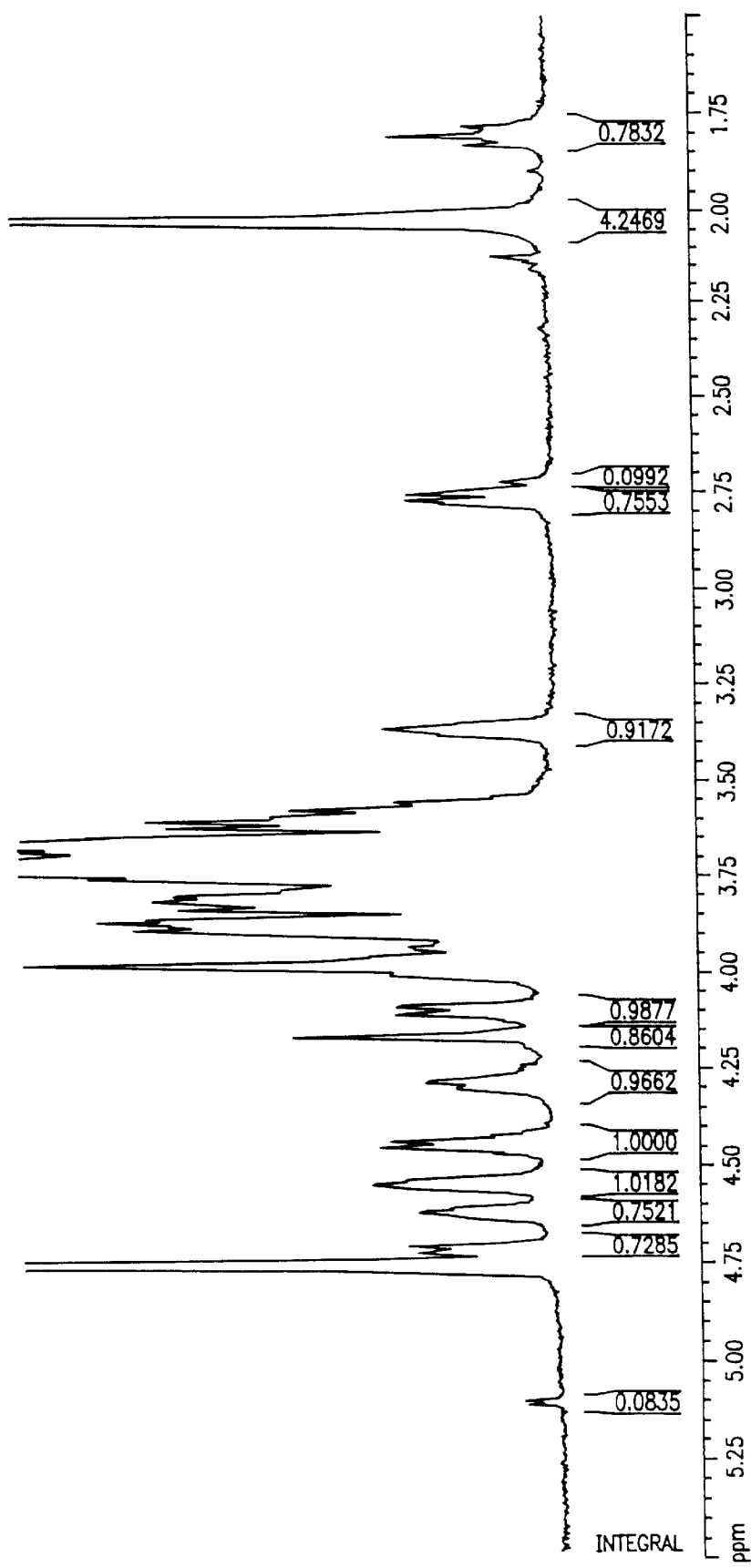
FIG. 6. H-NMR spectrum of GBS type III polysaccharide fragment having a molecular weight of approximately 9 kDa and showing the hydrogen peaks associated with the 2,5-anhydro-D-mannose prepared according to the method of this invention.

The binding of the rabbit GBS type II or III polysaccharide-specific antibodies to the various tetanus-toxoid conjugates are expressed in percent relative to the binding of the native type II or type III polysaccharide-tetanus-toxoid conjugates as illustrated in FIGS. 1 and 2 respectively.

Example 4

Immunization of Female Mice To Confer Protection Against GBS Infection In Neonatal Mice Female CD-1 mice (n=3), 6–8 weeks old, from Charles River Laboratories, Wilmington, Mass., were injected i.p. with two doses of conjugate vaccines (containing 2 μg (equalized for polysaccharide 1 μg/mouse) of polysaccharide-fragment (average MW about 11,000 Daltons) in Alhydrogel 1.3% (Superfos Biosector a/s, batch #2043), total volume 0.5 ml I.P.) on day 0 and 21. control mice (n=3) received vaccines containing 2 μg of native type III GBSCP. Mice were bred at day 21 and pups (<36 h old) were challenged i.p. with lethal doses of type III GBS M781 bacteria ($6 \times 10^5$ CFU). Survival was assessed 48 h after bacterial challenge.

As shown in Table IV vaccination of the female mice with GBS type III-TT conjugate prior to breeding conferred protection in 94% of the pups subsequently born to them.

TABLE IV

| Vaccine | No. of pups (No. of dams) | No. (%) Surviving 48 h |
|---|---|---|
| GBS III-TT | 33 (3) | 31 (94)+ |
| GBS III-PS | 39 (3) | 0 (0) |
| Saline | 34 (3) | 0 0 |

+Statistically significant (P < 0.0001) from control

Refs:

Lawrence C. Madoff et. al., *Infection and Immunity*, 60:4989–4994 (1992)

Rodewald, A. K., et. al., *Journal of Infectious Disease*, 166:635–639 (1992)

Although the invention has been described in conjunction with the specific embodiments, it is evident that many alternatives and variations will be apparent to those skilled in the art in light of the foregoing description. Accordingly, the invention is intended to embrace all of the alternatives and variations that fall within the spirit and scope of the appended claims. Further, the subject matter of the above cited United States Patents are incorporated herein by reference.

We claim:

1. A conjugate molecule comprising at least one polysaccharide fragment covalently bound to a protein wherein the at least one polysaccharide fragment is selected from the group consisting of Group B streptococcus type II and type III polysaccharide fragments, wherein the Group B streptococcus type II and/or type III polysaccharide fragment is obtained by a process comprising partial de-N-acetylation and depolymerization by deamination, and wherein the fragment is covalently bound to a protein wherein the conjugate molecule has the structure

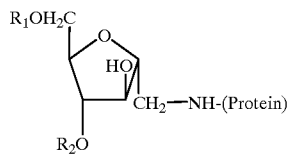

wherein for the type II fragment $R_1$ is H and $R_2$ is sialylated heptasaccharide repeating-unit of formula

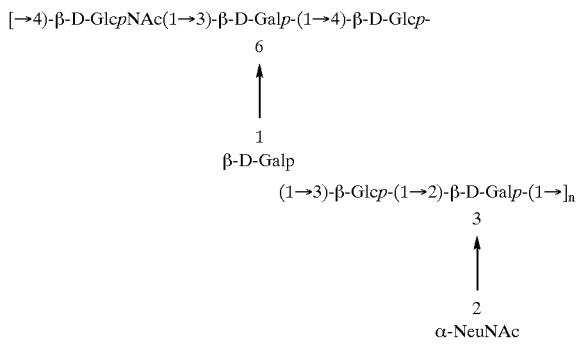

wherein n is about 5 to about 50, and where for the type III fragment $R_1$ is sialylated pentasaccharide repeating-unit of formula

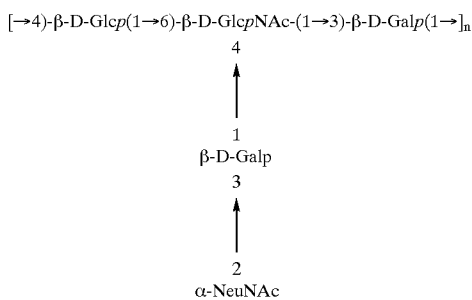

wherein n is about 5 to 50 and $R_2$ is a disaccharide αNemNAc(2-3)β-D-Galp↓-.

2. The conjugate molecule according to claim 1 wherein the protein is derived from a bacterium.

3. The conjugate molecule according to claim 2 wherein the protein is a bacterial protein selected from the group consisting of tetanus toxoid, diphtheria toxoid, $CRM_{197}$, a recombinant non-IgA biting protein of the β-C antigen of type Ia/Ib Group B streptococcus, and recombinant class 3 outer membrane protein from *Neisseria meningitides*.

4. The conjugate molecule according to claim 3 wherein the polysaccharide fragment is a Group B streptococcus type II polysaccharide fragment, the protein is tetanus toxoid ad the molecular weight of the polysaccharide fragment is between about 5 kDa and 50 kDa.

5. The conjugate molecule according to claim 3 wherein the polysaccharide fragment is a Group B streptococcus type III polysacchahide fragment, the protein is tetanus toxoid and the molecular weight of the polysaccharide fragment is between about 5 kDa and 50 kDa.

6. The conjugate molecule according to claim 3 wherein the polysaccharide fragment and the protein have a molar ratio of between about 1 and 10.

7. The conjugate molecule according to claim 6 wherein the polysaccharide fragment and the protein have a molar ratio of between about 3 and 10.

8. The conjugate molecule according to claim 1 comprising Group B streptococcus type II and type III polysaccharide fragments.

9. The conjugate molecule according to claim 8 wherein the protein is a recombinant non-IgA binding protein of the β-C antigen of type Ia/Ib Group B streptococcus.

10. A vaccine composition comprising at least one conjugate molecule comprising a Group B streptococcus type II and/or type III polysaccharide fragment covalently bound to a protein wherein the Group B streptococcus type II and/or type III polysaccharide fragment is obtained by a process comprising partial de-N-acetylation ad depolymerization by deamination, wherein the conjugate molecule has the structure

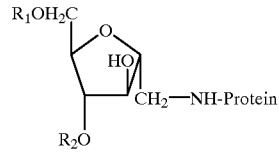

wherein for the type II fragment $R_1$ is H and $R_2$ is siaylated heptasaccharide repeating-unit of formula

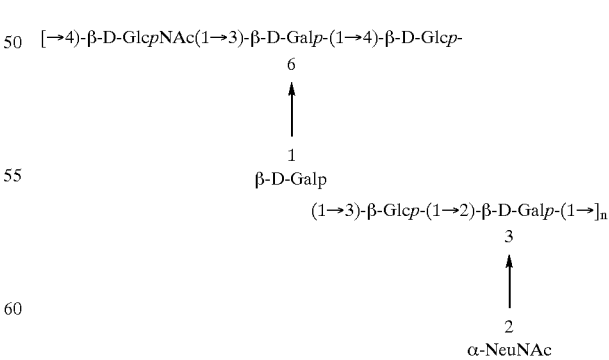

wherein n is about 5 to about 50, and where for the type III fragment $R_1$ is sialylated penitasaccharide repeating-unit of formula

[→4)-β-D-Glcp(1→6)-β-D-GlcpNAc-(1→3)-β-D-Galp(1→]$_n$

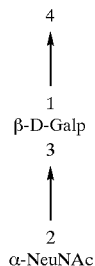

wherein n is about 5 to 50 and R$_2$ is a disaccharide αNemNAc(2-3)β-D-Galp↓-.

11. The vaccine composition according to claim 10 wherein the fragment is a Group B streptococcus type II polysaccharide fragment and the molecular weight of the polysaccharide fragment is between about 5 kDa and 50 kDa.

12. The vaccine composition according to claim 10 wherein the fragment is a Group B streptococcus type III polysaccharide fragment and the molecular weight of the polysacehide fragment is between about 5 kDa and 50 kDa.

13. The vaccine composition according to claim 10 wherein the protein is a bacterial protein selected from the group consisting of tetanus toxoid, diphtheria toxoid, CRM$_{197}$, a recombinant non-IgA binding protein of the β-C antigen of type Ia/Ib Group B streptococcus, and recombinant class 3 outer membrane protein from *Neisseria meningitides*.

14. The vaccine composition according to claim 13 wherein the protein is selected from the group consisting of a recombinant non-IgA binding protein of the β-C antigen of type Ia/Ib Group B streptococcus, and recombinant class 3 outer membrane protein from *Neisseria meningitides*.

15. The vaccine composition according to claim 10 comprising at least one conjugate molecule comprising Group B streptococcus type II and III polysacchaide fragments.

16. The vaccine composition according to claim 10 wherein the fragment is a Group B streptococcus type II polysaccharide fragment and the molecular weight of the polysaccharide fragment is between about 5 kDa and 50 kDa.

* * * * *

UNITED STATES PATENT AND TRADEMARK OFFICE
CERTIFICATE OF CORRECTION

PATENT NO.    : 6,372,222 B1
DATED         : April 16, 2002
INVENTOR(S)   : Francis Michon et al.

It is certified that error appears in the above-identified patent and that said Letters Patent is hereby corrected as shown below:

Column 4,
Lines 19-25, please delete "

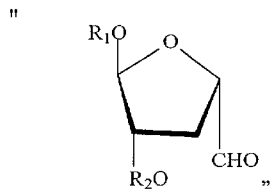

and insert therefor --

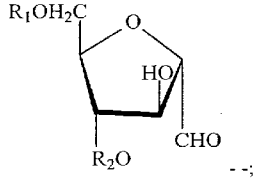

--;

Column 8,
Lines 26-35, please delete "

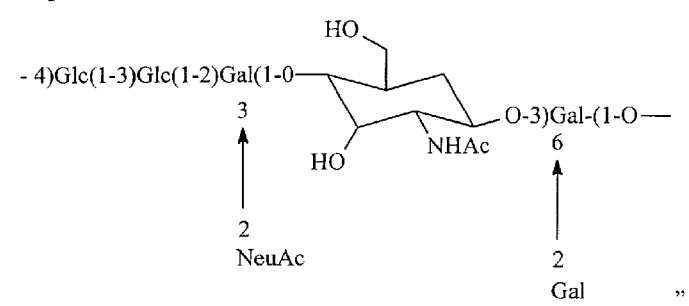

"

and insert therefor --

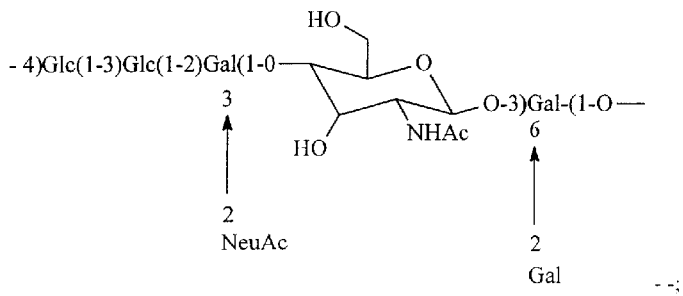

--;

UNITED STATES PATENT AND TRADEMARK OFFICE
CERTIFICATE OF CORRECTION

PATENT NO. : 6,372,222 B1
DATED : April 16, 2002
INVENTOR(S) : Francis Michon et al.

It is certified that error appears in the above-identified patent and that said Letters Patent is hereby corrected as shown below:

Column 9,
Line 46, please delete "multivalent:" and insert therefor -- multivalent --;

Column 14,
Line 40, please delete "21. control" and insert therefor -- 21. Control --;

Column 15,
Lines 8-9, please delete "covalently bound to a protein wherein the at least one polysaccharide fragment is"
Line 13, please delete "de-N-acetylation" and insert therefor -- de-*N*-acetylation --;
Line 21, please delete "(protein)" and insert therefor -- protein --;
Line 60, please delete "Galp" and insert therefor -- Galp1 --;

Column 16,
Line 3, please delete "ad" and insert therefor -- and --;
Line 34, please delete "de-N-acetylation ad" and insert therefor -- de-*N*-acetylation and --;
Line 66, please delete "penitasaccharide" and insert therefor -- pentasaccharide --;

Column 17,
Line 15, please delete "50and" and insert therefor -- 50 and --;
Line 16, please delete "Galp" and insert therefor -- Galp1 --;
Line 25, please delete "polysacehide" and insert therefor -- polysaccharide --;

Column 18,
Line 17, please delete "polysacchaide" and insert therefor -- polysaccharide --;

Signed and Sealed this

Twenty-ninth Day of October, 2002

*Attest:*

*Attesting Officer*

JAMES E. ROGAN
*Director of the United States Patent and Trademark Office*